United States Patent [19]

Draber et al.

[11] 4,141,981

[45] Feb. 27, 1979

[54] ANTIMICROBIAL AGENT

[75] Inventors: Wilfried Draber; Manfred Plempel; Karl H. Büchel; Erik Regel, all of Wuppertal, Fed. Rep. of Germany

[73] Assignee: Bayer Aktiengesellschaft, Leverkusen, Fed. Rep. of Germany

[21] Appl. No.: 813,055

[22] Filed: Jul. 5, 1977

[30] Foreign Application Priority Data

Jul. 6, 1976 [DE] Fed. Rep. of Germany ....... 2630252
Mar. 8, 1977 [DE] Fed. Rep. of Germany ....... 2709964

[51] Int. Cl.$^2$ ........................................... A61K 31/44
[52] U.S. Cl. ................................................ 424/263
[58] Field of Search ...................................... 424/263

[56] References Cited

U.S. PATENT DOCUMENTS 3,897,438    7/1975    Draber et al. .................. 424/263

FOREIGN PATENT DOCUMENTS 1298535  12/1977  United Kingdom .................. 424/263

*Primary Examiner*—Jerome D. Goldberg
*Attorney, Agent, or Firm*—Sprung, Felfe, Horn, Lynch & Kramer

[57] ABSTRACT

Antimycotic compositions in topical or vaginal administration form are prepared wherein the active agent is imidazol-1-yl-(4-phenoxyphenyl)-(pyridin-2-yl)phenylmethane in combination with a pharmaceutically acceptable carrier suitable for topical application to the skin of a human or suitable for vaginal administration to humans. Such compositions are useful for treating mycoses in humans.

6 Claims, No Drawings

ANTIMICROBIAL AGENT

The present invention is concerned with the use of imidazol-1-yl-(4-phenoxyphenyl)-(pyridin-2-yl)phenylmethane as an antimycotic.

Imidazol-1-yl-(4-phenoxyphenyl)-(pyridin-2-yl)phenylmethane is known from U.S. Pat. No. 3,897,438 which discloses a process for the production of this compound which is indicated to be useful as a fungicide, herbicide and plant growth control agent. The compound is also known from Belgium Pat. No. 765,585, German No. 2,016,839 and British Pat. No. 1,298,535 as an antiprotozoal agent.

The present invention is based on the surprising discovery that imidazol-1-yl-(4-phenoxyphenyl)-(pyridin-2-yl)phenylmethane of the formula:

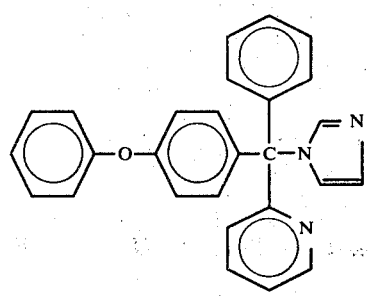

displays a high level of activity against mycotic infections in humans and is particularly suitable for the treatment of mycotic infections on the skin of humans by the topical application of said compound, and is additionally useful for the treatment of mycotic infections in humans by vaginal administering said compound in combination with a pharmaceutically acceptable carrier suitable for said administration form.

It is known in the art that certain N-diaryl-pyridyl-methyl imidazoles such as N-diphenyl-(pyridin-2-yl)-methyl imidazole are useful as antimycotics (see German OLS 1,770,939).

Imidazol-1-yl-(4-phenoxyphenyl)-(pyridin-2-yl)phenylmethane of the formula:

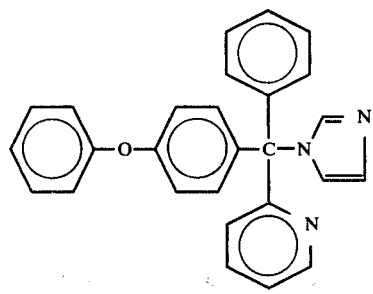

displays good antimicrobial, and especially antimycotic, properties when it is combined with a pharmaceutically acceptable carrier which is suitable for topical application to the skin of a human. In addition, the compound is useful for the treatment of mycotic infections in humans when it is combined with a pharmaceutically acceptable carrier suitable for vaginal administration to humans and administered vaginally to humans. In particular, it has been found that the pharmaceutical compositions according to the present invention and the methods of treating mycotic infections in humans utilizing the pharmaceutical compositions of the present invention are not only advantageous because of the residence time on the skin in relation to the antimycotic effect but because the antimycotic activity is, on a residence time on human skin bases, superior to the known antimycotic agent Clotrimazol so that its spectrum of activity is approximately equal to Clotrimazol while its intensity of action is superior to this commercially valuable product.

In addition, the pharmaceutical compositions according to the present invention have sporocidal action against microconidia and macroconidia of Trichophyton and Microsporum species in concentrations at a level at which Clotrimazol does not exhibit sporocidal activity.

Imidazol-1-yl(4-phenoxyphenyl)-(pyridin-2-yl)phenylmethane may be produced according to the process disclosed in the prior art such as, for example, by reacting (4-phenoxyphenyl)-phenyl-(pyridin-2-yl)chloromethane in a polar solvent with an excess of imidazole at a temperature of from about 80° C. to about 100° C.

The pharmaceutical compositions of the present invention have a broad antimycotic spectrum of activity and exhibit good activity against Dermatophytes and Yeasts as well as biphase fungi, such as Candida, particularly *Candida albicans*, Epidermophyton, such as *Epidermophyton floccosum*, Aspergillus, such as *Aspergillus niger*, Trichophyton, such as *Trichophyton mentagrophytes*, Microsporum, such as *Microsporum felineum*, and Penicillium, such as *Penicillium commune*.

Thus the pharmaceutical compositions of the present invention are particularly useful in the treatment of dermatomycoses and systemic mycoses in humans caused by *Trichophyton mentagrophytes* and other species of Trichophyton, Microsporum, *Epidermophyton floccosum*, Yeasts and biphase fungi, as well as moulds.

According to the present invention, antimycotic compositions are prepared in a form suitable for topical application to the skin of a human which comprises an antimycotically effective amount of imidazol-1-yl(4-phenoxyphenyl)-(pyridin-2-yl)phenylmethane in combination with a pharmaceutically acceptable carrier suitable for topical administration form to the skin of a human. The pharmaceutical compositions may be in ointment, paste, cream or gel form or may be in the form of a powder or spray. The pharmaceutical acceptable carrier is thus one which is suitable for the formation of an ointment, paste, cream, gel, powder or spray to be applied to the skin of a human. Thus, for example, the pharmaceutical compositions of the present invention may contain, in addition to the antimycotically active agent, animal and vegetable fats, waxes, paraffins, starch, tragacanth, cellulose derivatives, polyethylene glycols, silicones, bentonites, silica, talc, zinc oxide or mixtures of these substances and in the case of powders or sprays may contain the customary excipients such as lactose, talc, silica, aluminium hydroxide, calcium silicate, polyamide powders, or mixtures thereof. When the pharmaceutical composition is in the form of a spray, any customary propellant which is compatible with the skin of a human may be used.

In addition, the antimycotic compositions of the present invention may be formulated in a form suitable for vaginal administration to a human and in such a case, they are suitably formulated into vaginal tablet form so that the pharmaceutically acceptable carrier is one suitable for combination with the active agent to form a vaginal tablet suitable for administration to humans. When the pharmaceutical compositions of the present invention are in vaginal tablet form, such compositions may contain in addition to the active agent the usual excipients such as lactose, magnesium stereate, adipic acid, sodium carbonate, sodium bicarbonate or mixtures thereof.

When the pharmaceutical compositions of the present invention are in topical application form, they may additionally be in the form of solutions or emulsions and in such an event may contain the usual excipients such as suitable solvents, solubilizing agents and emulsifiers such as water, ethyl alcohol, isopropyl alcohol, ethyl carbonate, ethyl acetate, benzyl alcohol, benzyl benzoate, propylene glycol, 1,3-butylene glycol, dimethylformamide, oils such as cottonseed oil, groundnut oil, maize germ oil, olive oil, castor oil, sesame oil, glycerol, glycerol-formal, tetrahydrofurfuryl alcohol, polyethylene glycols, fatty acid esters of sorbitane, or mixtures thereof.

According to the pharmaceutical compositions above described the active agent should be present in a concentration of 0.1 to 99.5%, and preferably from about 0.5 to 95%, by weight of total composition. More specifically, the active agent should be present in a concentration of about 0.1 to 5%.

The pharmaceutical compositions of the present invention are prepared according to techniques known per se in the pharmaceutical industry such as by mixing the active agent with the pharmaceutically acceptable carrier and any additional excipient or excipients.

While the precise amount of the active agent will depend upon the precise condition being treated as well as the present and past medical history of the patient, it is generally advantageous to administer to a human an amount of from about 10 to about 300 mg/kg per day, and preferably from about 50 to 200 mg/kg of active agent.

The following examples are illustrative of the antimycotic activity in humans.

EXAMPLE A

Antimycotic in vitro activity

Description of the experiment:

In vitro experiments were carried out using a serial dilution test on yeast morphology medium and Nervina nutrient solution. The serial dilution contained the active compound in concentrations of 0.062, 0.125, 0.25, 0.5, 1, 2, 4, 8, 16, 32 and 64 mcg/ml of substrate and were incubated at 28° C. for 24–96 hours. Readings were taken by comparison with untreated control cultures of the fungi tested. The inocula were $1 \times 10^5$ germs/ml in the case of yeasts and $1 \times 10^4$ germinative particle/ml in the case of dermatophytes and moulds.

The minimal inhibitory concentrations (MIC) for representative species of fungi pathogenic to humans are set forth in Table A below:

Table A:

| Active compound | Antimycotic in vitro activity Minimum inhibitory concentration in γ/ml of nutrient medium | | | |
| --- | --- | --- | --- | --- |
| | Trich. ment. | Cand. alb. | Asperg. niger | Microsp. fel. |
| 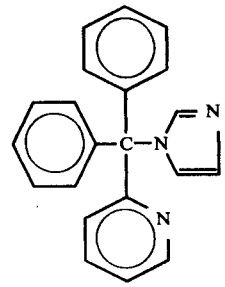 (known) | <4 | 40 | 10 | 10 |
| 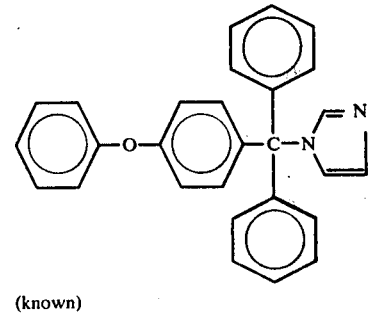 (known) | 4 | >100 | >100 | 40 |

Table A:-continued

| Active compound | Antimycotic in vitro activity Minimum inhibitory concentration in γ/ml of nutrient medium | | | |
|---|---|---|---|---|
| | Trich. ment. | Cand. alb. | Asperg. niger | Microsp. fel. |
| [structure: phenoxyphenyl-phenyl-pyridyl-C-N-imidazole] | 0.125 | <1 | <1 | <1 |

EXAMPLE B

Antimycotic in vivo activity (oral) in the mouse Candidose

Experimental Description:

Male white mice ($CF_1$-spf, 20–22 g weight, Ssniffpellet-feed and water ad libitum, cage temperature 21°–22° C.) were infected by puncture in the tail vein with 1 to $5 \times 10^6$ Candida albicans cells in 0.2 ml physiological NaCl solution i.v.

The active agent of the invention was dispensed with a probang to the test animals two hours before infection and six hours after infection and in the succeeding days twice daily in doses of 100 mg/kg of body weight orally.

In Table B the results after three days p.i. were collected. Twenty mice were used per each group. The figures given are median values of two like tests.

Table B:

| Active compound | Antimycotic in vivo activity (oral) against candidosis in mice | |
|---|---|---|
| | Dose in mg/kg Kg/day | Number of dead animals after 3 days after infection |
| Untreated control | — | 13/20 = no action |
| [structure: diphenyl-pyridyl-C-N-imidazole] (known) | 2 × 100 | 14/20 = no action |
| [structure: phenoxyphenyl-phenyl-pyridyl-C-N-imidazole] (known) | 2 × 100 | 6/20 = action |

Table B:-continued

Antimycotic in vivo activity (oral) against candidosis in mice

| Active compound | Dose in mg/kg Kg/day | Number of dead animals after 3 days after infection |
|---|---|---|
| 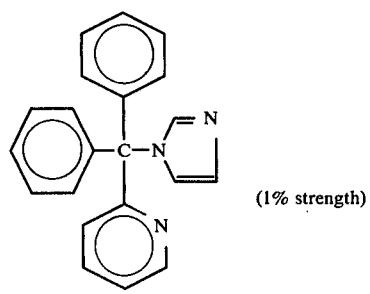 | 2 × 100 | 2/20 = good action |

EXAMPLE C

Antimycotic activity in vivo when administered topically to guinea-pigs infected with Trichophyton Experimental arrangement:

The backs of white guinea-pigs of the "Pirbright-white" breed weighing 450–600 g (Altromin pellet feed, hay, carrots and water ad libitum, cage temperature 21°–22° C.) are so shorn with an electrical haircutting machine that hair stumps about 0.1 cm in length remain. 1 day later — after the minor skin irritations have subsided — the animals are infected on a 2 × 2 cm area on the back with a spore suspension of Trichophyton mentagrophytes or *Trichophyton rubrum* which contains 1 × 10⁵ germinative particles per ml, by rubbing in the infective agent lightly into the skin.

3 days later, after the first indications of infection, in the form of inflammatory reactions of the skin, had arisen, the animals were treated once daily, up to the 14th day after infection, with a 0.1 or 1% strength solution of the active compound according to the invention by applying 0.5 ml of the formulation solution and rubbing it lightly into the infected area with a horn spatula.

The activity was assessed according to a number system in which

- 0 denotes no sign of infection
- 1 denotes reddening of the skin
- 2 denotes reddening of the skin and peripheral scaling
- 3 denotes scaling and incipient loss of hair
- 4 denotes extensive patchy loss of hair with an incipient integumentary defect and
- 5 denotes patchy, bleeding integumentary defect.

Table C:

Antimycotic activity in vivo upon topical application to guinea-pigs infected with Trichophyton

| Active compound (concentration) | Course of the infection after | | | | | | |
|---|---|---|---|---|---|---|---|
| | 3 | 5 | 7 | 9 | 11 | 13 | 15 days after infection |
| Control (average value for 20 animals) | 1 | 2/3 | 3/4 | 4 | 4/5 | 5 | 5 |
| | 1 | 1 | 1 | 1/2 | 2 | 2/3 | 2/3 |
| 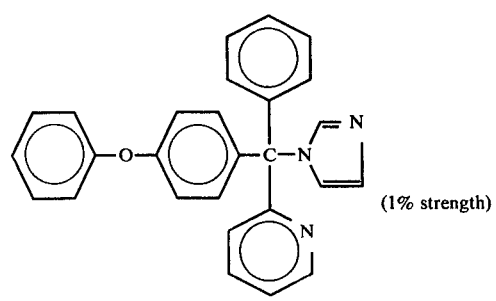 (1% strength) (known) = action | | | | | | | |
| | 1 | 1 | 1/2 | 2 | 2 | 2/3 | 3/4 |
| (1% strength) (known) = slight action | | | | | | | |

Table C:-continued

Antimycotic activity in vivo upon topical application to guinea-pigs infected with Trichophyton

| Active compound (concentration) | Course of the infection after |  |  |  |  |  |  |
|---|---|---|---|---|---|---|---|
| | 3 | 5 | 7 | 9 | 11 | 13 | 15 days after infection |

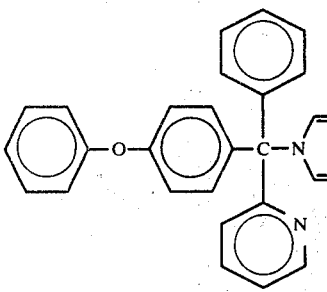

(1% strength)
(average value for 40 animals)

| | 1 | 1 | 0/1 | 0/1 | 0/1 | 0 | 0 |

(0.1% strength)
(average value for 20 animals)

| | 1 | 1 | 1/2 | 1/2 | 2 | 2 | 2/3 |

≒ very good action
= action

EXAMPLE D

Sporocidal action

In concentrations of >10 mcg/ml of substrate imidazol-1-yl-(4-phenoxyphenyl)-(pyridin-2-yl)-phenylmethane has a partial (up to 60%) sporocidal action against microconidia and macroconidia of Trichophyton species and Microsporum, species and with 100 mcg/ml has a local (100%) sporocidal action against microconidia and macroconidia of the said species. Clotrimazol does not have a sporocidal action in these concentrations.

EXAMPLE E

Residence time on the skin

Measured by its protective action against infection in infected guinea-pigs, imidazol-1-yl-(4-phenoxyphenyl)-(pyridin-2-yl)-phenylmethane (I) has a residence time on the skin of >48-60 hours. In the same experiment Clotrimazol has a residence time on the skin of >24-30 hours.

This surprisingly long residence time on the skin makes it possible to reduce the frequency of application per 24 hours from 3 times in the case of Clotrimazol to once in the case of I. The reliability of therapy is to be regarded as very much greater in the case of I. Moreover, in severe cases a cumulation of active compound in the skin, that is to say the point of infection, can be achieved by application 2-3 times daily and this further increases the reliability and effectiveness of therapy.

Together with the sporocidal activity, the long residence time on the skin, which can be influenced in a cumulative manner, can lead to a highly desirable shortening in the period of therapy: the therapy period, without fear of relapse, is foud to be about 14 days in the case of dermatophytoses (4-6 weeks with Clotrimazol) and 2-3 days in the case of vaginal candidoses and Torulopsis infections of the vagina (from 6 days with Clotrimazol).

Preparation example

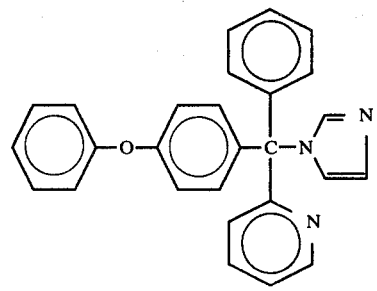

88.2 g (0.025 mol) of 4-phenoxyphenyl-phenyl-(pyridin-2-yl)-carbinol are dissolved in 500 ml of methylene chloride and 32.5 g (0.27 mol) of thionyl chloride are added. The mixture is heated until the evolution of gas has ceased (about 10 minutes) and concentrated in vacuo. The oily residue is added to a boiling solution of 51.3 g (0.75 mol) of imidazole in 250 ml of anhydrous acetonitrile. The mixture is heated for a further 30 minutes and the solvent is then stripped off in vacuo. The residue is taken up in 1,000 ml of ethyl acetate and the organic phase is extracted several times by shaking with water and dried with sodium sulphate. The imidazole derivative is then precipitated in the form of the hydrochloride by passing in hydrogen chloride. The salt which has precipitated is dried, ground to a powder and slowly added to a solution of 42 g (0.5 mol) of sodium bicarbonate in 2 l of water. After stirring for some time, the product precipitates as crystals. These are filtered off, washed with water, dried and recrystallised from ethyl acetate. This gives 50.8 g (50.4% of theory) of (imidazol-1-yl)-(4-phenoxyphenyl)-phenyl-(pyridin-2-yl)-methane as pale yellowish crystals with a melting point of 137°-140° C.

Preparation of the starting material

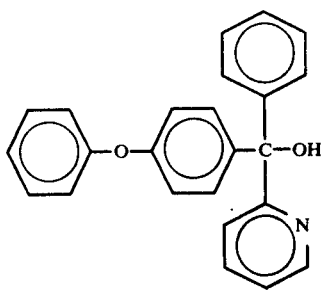

249 g (1 mol) of 4-bromodiphenyl ether are reacted with 29 g (1 mol) of magnesium in 0.5 l of ether in the customary manner to give the corresponding Grignard compound. This solution is added to 174 g (0.95 mol) of phenyl-(pyridin-2-yl) ketone in 0.5 l of ether, while stirring vigorously. The mixture is stirred for some hours more and 300 ml of concentrated hydrochloric acid and 300 ml of water are then added. Three phases form. The ether phase is separated off, dried and concentrated. This gives about 25 g of a solid residue. The heavy phase, which is a viscous oil, contains the hydrochloride of the carbinol. It is separated off and added dropwise to aqueous sodium hydroxide solution. The carbinol precipitates as a solid. It is filtered off and dried and recrystallised, together with the residue from the ether phase, from ethyl acetate/ligroin. This gives 130 g (39% of theory) of 4-phenoxyphenyl-phenyl-(pyridin-2-yl)-carbinol in the form of colorless crystals with a melting point of 114° C.

What is claimed is:

1. A method of treating a spore-forming mycotic infection in humans and animals which comprises topically applying to the skin of said human or animal in need of said treatment a topical composition comprising a sporicidally effective amount of a compound of the formula:

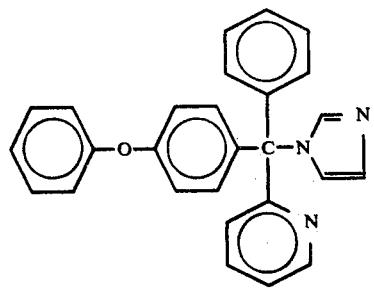

in combination with a pharmaceutically acceptable carrier suitable for topical application and in a concentration of about 0.1 to 5% active ingredient.

2. A method of claim 1 wherein the topical composition is in ointment form.

3. A method of claim 1 wherein the topical composition is in paste form.

4. A method of claim 1 wherein the topical composition is in the form of a cream.

5. A method of claim 1 wherein the topical composition is in the form of a gel.

6. A method of claim 1 wherein the infection is in the vaginal tract.

* * * * *